(12) United States Patent
Kobayashi

(10) Patent No.: US 8,831,710 B2
(45) Date of Patent: Sep. 9, 2014

(54) MEDICAL OBSERVATION SYSTEM AND PROCESSOR

(75) Inventor: Shotaro Kobayashi, Toko (JP)

(73) Assignee: Hoya Corporation, Tokyo (JP)

(*) Notice: Subject to any disclaimer, the term of this patent is extended or adjusted under 35 U.S.C. 154(b) by 303 days.

(21) Appl. No.: 12/834,169

(22) Filed: Jul. 12, 2010

(65) Prior Publication Data

US 2011/0015528 A1  Jan. 20, 2011

(30) Foreign Application Priority Data

Jul. 15, 2009 (JP) ................................. 2009-166880

(51) Int. Cl.
*A61B 5/00* (2006.01)
*A61B 1/00* (2006.01)
*A61B 1/07* (2006.01)
*G02B 23/24* (2006.01)

(52) U.S. Cl.
CPC ........... *A61B 5/0059* (2013.01); *A61B 1/00057* (2013.01); *A61B 1/07* (2013.01); *A61B 1/00172* (2013.01); *A61B 5/0062* (2013.01); *A61B 5/0084* (2013.01); *G02B 23/2469* (2013.01); *G02B 23/2476* (2013.01)
USPC ............ 600/478; 600/475; 600/477; 600/117

(58) Field of Classification Search
USPC .................................. 600/117, 475, 477, 478
See application file for complete search history.

(56) References Cited

U.S. PATENT DOCUMENTS

| | | | | |
|---|---|---|---|---|
| 5,154,707 A * | 10/1992 | Rink et al. | | 606/12 |
| 5,957,834 A * | 9/1999 | Mochida | | 600/180 |
| 6,294,775 B1 * | 9/2001 | Seibel et al. | | 250/208.1 |
| 6,364,827 B1 * | 4/2002 | Irion et al. | | 600/118 |
| 6,370,422 B1 * | 4/2002 | Richards-Kortum et al. | 600/478 |
| 6,468,204 B2 * | 10/2002 | Sendai et al. | | 600/160 |
| 6,511,422 B1 * | 1/2003 | Chatenever | | 600/180 |
| 6,767,320 B2 * | 7/2004 | Farkas et al. | | 600/108 |
| 7,440,661 B2 * | 10/2008 | Kobayashi | | 385/117 |
| 7,556,414 B2 * | 7/2009 | Hopkins et al. | | 362/574 |
| 7,953,261 B2 * | 5/2011 | Nishimura et al. | | 382/128 |
| 8,346,347 B2 * | 1/2013 | Altshuler et al. | | 600/476 |
| 2005/0279354 A1* | 12/2005 | Deutsch et al. | | 128/200.24 |
| 2006/0009679 A1* | 1/2006 | Ito et al. | | 600/117 |
| 2006/0020169 A1* | 1/2006 | Sugimoto | | 600/180 |
| 2008/0132886 A1* | 6/2008 | Cohen et al. | | 606/34 |
| 2009/0221875 A1* | 9/2009 | Kobayashi | | 600/180 |
| 2009/0316144 A1* | 12/2009 | Kobayashi | | 356/239.2 |
| 2010/0049055 A1* | 2/2010 | Freudenberg et al. | | 600/475 |
| 2010/0177368 A1* | 7/2010 | Kobayashi | | 359/198.1 |
| 2010/0179386 A1* | 7/2010 | Kobayashi | | 600/178 |

* cited by examiner

*Primary Examiner* — Long V. Le
*Assistant Examiner* — Angela M Hoffa
(74) *Attorney, Agent, or Firm* — Greenblum & Bernstein, P.L.C.

(57) ABSTRACT

A medical observation system, which includes a medical probe that observes a subject by scanning on the subject with laser light; a laser source that supplies the laser light to the medical probe; a judgment unit that judges whether the medical probe is in a predetermined state; and a control unit that controls an amount of laser light emitted from the laser source based on a judgment result by the judgment unit.

14 Claims, 11 Drawing Sheets

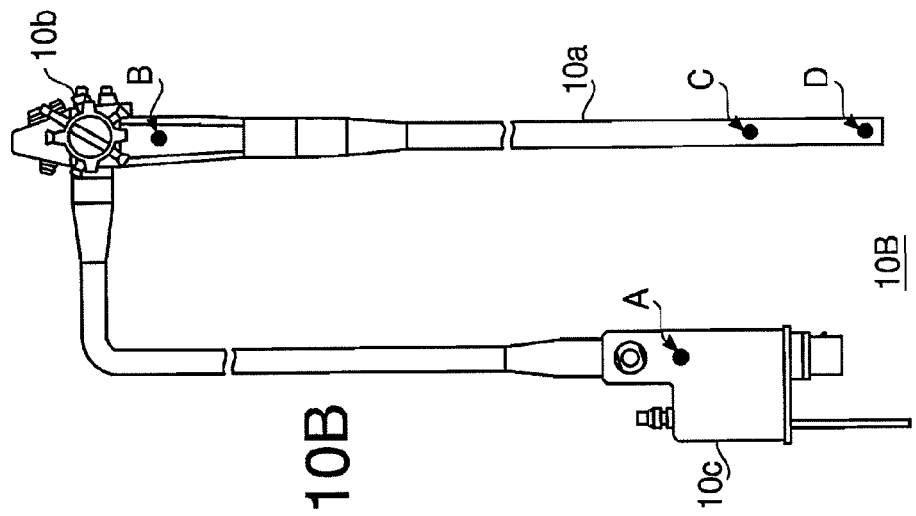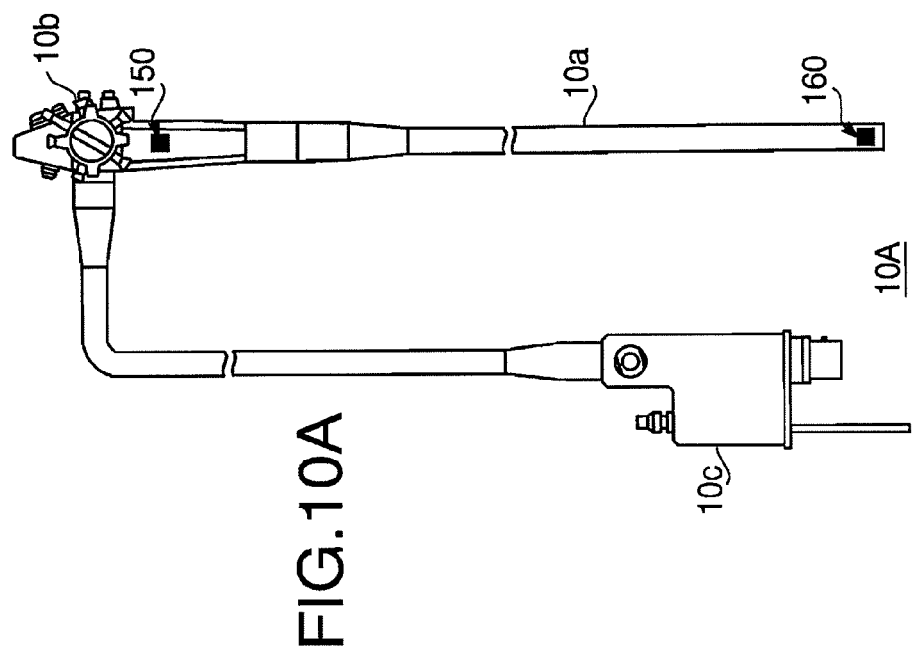

MEDICAL OBSERVATION SYSTEM AND PROCESSOR

BACKGROUND OF THE INVENTION

The present invention relates to a medical observation system using a scanning medical probe for obtaining image information by scanning a subject, and to a processor for the scanning medical prove.

In general, an electronic-scope is used when a doctor observes a body cavity of a patient. The doctor inserts an electronic-scope into a body cavity of a patient, and guides a tip part of an insertion unit of the electronic-scope to an area around an observation target. Then, an image in the body cavity is shot with a solid state imaging device, such as a CCD (Charge Coupled Device), installed in the tip part of the electronic-scope. The image shot by the solid state imaging device in the body cavity is then transmitted from the electronic-scope to a video processor. In the video processor, the received image is subjected to a predetermined imaging process, and the processed image is then displayed on a monitor. By observing the image displayed on the monitor, the doctor conducts medical diagnosis and treatment.

Recently, to ease a patient's suffering by insertion of an insertion unit of an electronic-scope, a medical probe formed to slenderize an outer diameter thereof, relative to the electronic-scope, by removing a component, such as a solid state imaging device, has been proposed. An observation system employing such a medical probe has also been proposed.

An example of such a medical probe is disclosed in U.S. Pat. No. 6,294,775 (hereafter, referred to as U.S. Pat. No. 6,294,775). The medical probe disclosed in U.S. Pat. No. 6,294,775 is configured to produce resonance on a tip of a single optical fiber to scan on a subject with scanning light. Then, reflected light from the subject is detected and the reflected light is subjected to photoelectric conversion. The converted signal is sequentially output to a video processor. The video processor processes the converted signal to display an image on a monitor. Thus, a doctor is able to conduct medical diagnosis and treatment while observing the obtained image in a body cavity of a patient as in the case of the electronic-scope.

SUMMARY OF THE INVENTION

Regarding the above described medical probe, laser light is used as the scanning light which is emitted from a tip of an optical fiber. Since the scanning light is emitted toward the subject after transmitting through a single optical fiber, the scanning laser light is required to have a highish intensity to obtain an image sufficient for observation of the body cavity. Since in general laser light may do harm to a human's eye when a human directly looks at the laser light, there are safety standards regarding the light amount of laser light with respect to a device which emits laser light, for example, in JIS (Japanese Industrial Standard).

In general, the medical probe is designed on the assumption that laser light is emitted in a condition where the medical probe is directly inserted into the body cavity or is indirectly inserted into the body cavity through a forceps channel of the electronic-scope. That is, the medical probe is not designed on the assumption that there is a possibility that laser light might directly enter an eye of a doctor or a patient. Hence, there may be a case where the medical probe in a state of emitting laser light is placed in an examination room, and therefore a possibility arises that the laser light directly enters an eye of a person in the examination room, such as an operator or a patient.

The present invention is advantageous in that it provides a medical observation system which is capable of limiting the amount of laser light to a safety level in a state where there is a possibility that the laser light directly enters an eye of a person, such as an operator.

According to an aspect of the invention, there is provided a medical observation system, which includes a medical probe that observes a subject by scanning on the subject with laser light; a laser source that supplies the laser light to the medical probe; a judgment unit that judges whether the medical probe is in a predetermined state; and a control unit that controls an amount of laser light emitted from the laser source based on a judgment result by the judgment unit.

With this configuration, it becomes possible to appropriately control the amount of laser light in accordance with whether the medical probe is inserted in the body. Furthermore, when it is judged that the medical probe is not inserted into the body, the amount of laser light is limited to a safety level and thereby it becomes possible to conduct observation for a body cavity while securing safety even when the laser light emitted from the medical probe directly enters an eye of a person in an examination room such as an operator.

In at least one aspect, the predetermined state may be a state where the medical probe is not inserted into a body. In at least one aspect, the control unit may control the laser source to reduce the amount of laser light emitted from the laser source when the judgment unit judges that the medical probe is in the predetermined state.

In at least one aspect, the control unit may reduce the amount of laser light emitted from the laser source in incremental steps based on the judgment result by the judgment unit. With this configuration, it becomes possible to reduce the amount of laser light by a required amount, and thereby it becomes to control appropriately and flexibly the amount of laser light in response to various conditions.

In at least one aspect, the medical probe may include: a light guiding member that guides the laser light to emit the laser light toward the subject; an oscillating unit that causes a part of the light guiding member around an exit end face of the light guiding member to oscillate, so as to scan on the subject with the laser light; and a light-receptive member that receives reflected light from the subject.

In at least one aspect, the judgment unit may judge whether the medical probe is in the predetermined state based on the reflected light received by the light-receptive member.

In at least one aspect, the judgment unit may judge that the medical probe is in the predetermined state when a light amount of the reflected light received by the light-receptive member is larger than a predetermined light amount. In at least one aspect, the judgment unit may judge that the medical probe is in the predetermined state when the reflected light blinks at a frequency which falls within a predetermined frequency range. With this configuration, it becomes possible to effectively judge the state of the medical probe based on the reflected light.

In at least one aspect, the judgment unit may judge whether the medical probe is in the predetermined state based on the reflected light which is received by the light-receptive member during a period in which the laser light is not emitted toward the subject. With this configuration, it becomes possible to judge the state of the medical probe based on light received by the light-receptive member other than the laser light.

In at least one aspect, the judgment unit may judge that the medical probe is in the predetermined state when an intensity of a signal based on the reflected light received by the light-receptive member does not change. With this configuration, it becomes possible to judge the state of the medical probe more accurately.

In at least one aspect, the medical probe may include at least one sensor that detects a condition of a use environmental of the medical probe. In this case, the judgment unit may judge whether the medical probe is in the predetermined state based on a detection result by the sensor. With this configuration, it becomes possible to reduce the processing load, such as signal processing, and thereby it becomes possible to execute the light amount control more quickly.

In at least one aspect, the at least one sensor may include: a humidity sensor provided at a tip of the light guiding member; and a contact sensor provided at a grip part of the medical probe. In this case, the judgment unit may judge whether the medical probe is in the predetermined state based on detection results by the humidity sensor and the contact sensor.

In at least one aspect, the at least one sensor includes a plurality of temperature sensors. In this case, the judgment unit may judge whether the medical probe is in the predetermined state based on a difference between temperatures detected by the plurality of temperature sensors.

According to another aspect of the invention, there is provided a processor for supplying laser light to a medical probe which observes a subject by scanning on the subject with the laser light. The processor includes a laser source that emits the laser light; a judgment unit that judges whether the medical probe is in a predetermined state; and a control unit that controls an amount of laser light emitted from the laser source based on a judgment result by the judgment unit.

With this configuration, it is possible to limit the amount of laser light to a safety level and thereby it becomes possible to conduct observation for a body cavity while securing safety even when the laser light emitted from the medical probe directly enters an eye of a person an examination room such as an operator.

BRIEF DESCRIPTION OF THE ACCOMPANYING DRAWINGS

FIG. 10A illustrates an outer appearance of a scanning medical probe according to a fourth embodiment of the invention, and FIG. 10B illustrates an outer appearance of a scanning medical probe according to a fifth embodiment of the invention.

DETAILED DESCRIPTION OF THE EMBODIMENTS

Hereinafter, embodiments according to the invention are described with reference to the accompanying drawings.

First Embodiment

Figure 1:
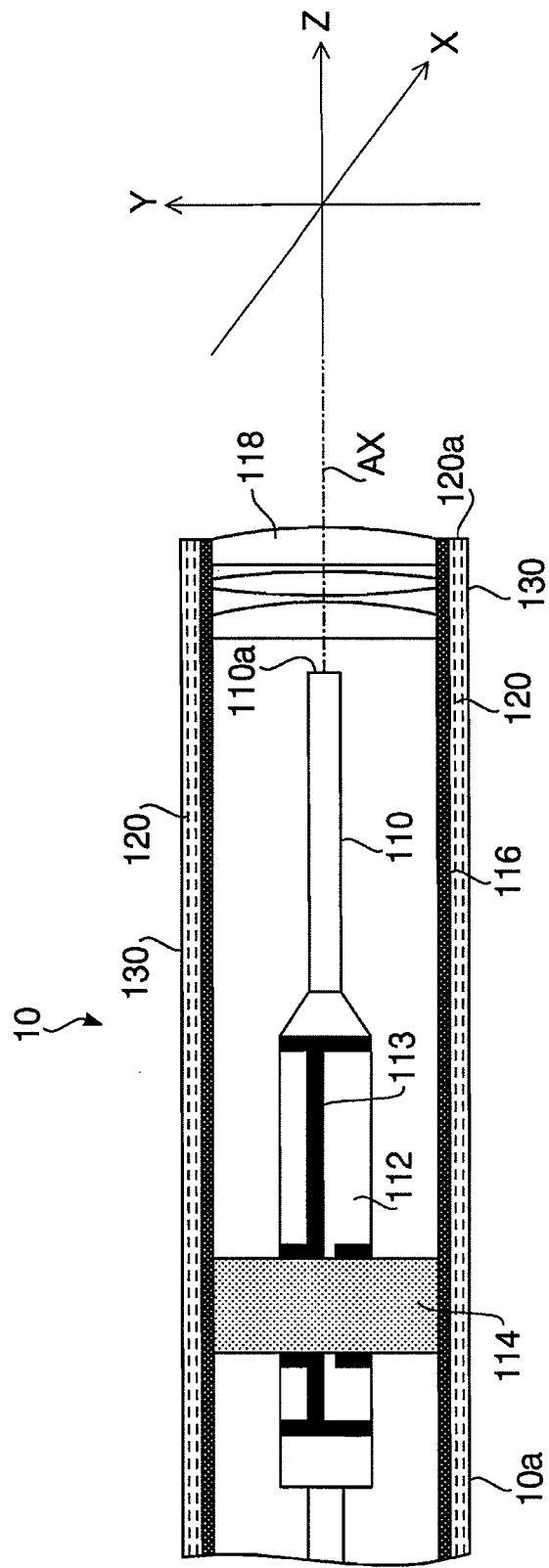
FIG. 1 illustrates an inner configuration of a tip part of a scanning medical probe according to an embodiment of the invention.
Figure 2:
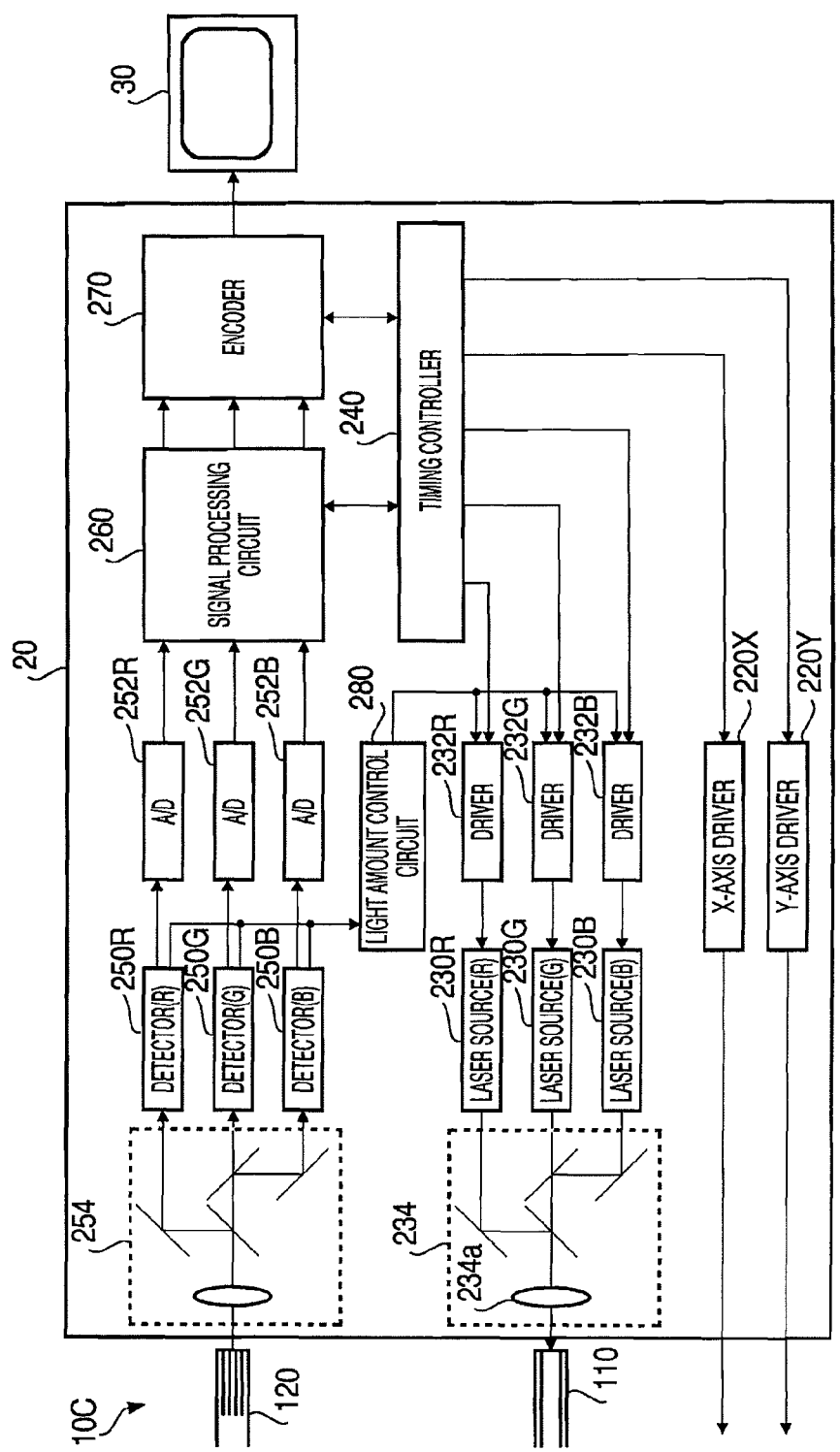
FIG. 2 is a block diagram of illustrating a configuration of a processor connected to the scanning medical probe according to the embodiment of the invention.

FIG. 1 illustrates an inner configuration of a tip part of a scanning medical probe 10 according to a first embodiment of the invention. FIG. 2 is a block diagram illustrating a configuration of a processor 20 to which the scanning medical probe 10 is connected. In FIG. 2, a part of the scanning medical probe 10 and a monitor 30 are also illustrated for clearly indicating connection relationship between the processor 20, the scanning medical probe 10 and the monitor 30. A monitor having a general configuration known in the art may be used as the monitor 30. The scanning medical probe 10, the processor 20 and the monitor 30 configure a medical observation system 1.

First, the configuration of the scanning medical probe 10 is explained with reference to FIG. 1. The scanning medical probe 10 includes an insertion unit 10a, a grip part 10b (see FIG. 10) to be gripped by an operator and a joint part 10c (see FIG. 2) to be electrically and optically connected to the processor 20. It should be noted that FIG. 1 illustrates a tip part of the insertion unit 10a of the scanning medical probe 10, and in the tip part a single mode fiber 110 (hereafter, referred to as an SMF 110), a cylindrical actuator 112, a support member 114, a housing 116, and a lens unit 118 are arranged. These components in the tip part of the insertion unit 10a are accommodated in an elastic sheath 130 serving as a protection tube. Furthermore, in the sheath 130, a plurality of light-receptive fibers 120 are buried in a circular shape.

The SMF 100 serves to transmit scanning light supplied from the processor 20 to a body cavity, and is arranged in the scanning medical probe 10 to extend from the joint part 10c to the tip of the insertion unit 10a. A tip part of the SMF 100 is inserted into a through hole formed in the actuator 112 in a longitudinal direction, and is fixed to the actuator 112, for example, with an adhesive.

The actuator 112 is formed of a piezoelectric device, and includes a plurality of electrodes 113. By supplying driving voltages from an X-axis driver 220X and a Y-axis driver 220Y (see FIG. 2) provided in the processor 20 to the electrodes 113 of the actuator 112 through conductive wires (not shown) connected to the electrodes 113, the actuator 112 starts to produce predetermined oscillation. The actuator 112 is supported in the state where the actuator 112 has passed through the through hole of the support member 114. Specifically, the tip part of the SMF 110 is supported by the support member 114 in a state of a cantilever beam. In the following, the longitudinal direction of the scanning medical probe 10 is defined as Z-direction, and directions which are orthogonal to the Z direction and are orthogonal to each other are defined as X direction and Y direction.

The housing 116 is a cylindrical member made of metal, such as stainless. The housing 116 serves to fix the lens unit 118 and the support member 114, and to protect the components located around the tip part of the scanning medical probe 10. The lens unit 118 includes a plurality of lenses, and functions as an optical system which converges the scanning light emitted from an exit end face 110a of the SMF 110 onto an observation target.

The light-receptive fibers 120 buried in the sheath 130 receive light reflected from the observation target through an entrance end face 120a. The light-receptive fibers 120 are arranged to extend in the scanning medical probe 10 from the joint part 10c to the tip of the insertion unit 10a. The reflected light received by the light-receptive fibers 120 is transmitted through the light-receptive fibers 120, and is coupled at the joint part 10c of the scanning medical probe 10 to be transmitted to the processor 20.

In this embodiment, the scanning medical probe 10 is directly inserted into a body cavity of a patient to observe the body cavity of the patient. However, in another embodiment, the insertion unit 10a of the scanning medical probe 10 may be inserted into the body cavity while being guided by a guide wire so that the tip part of the scanning medical probe 10 can be smoothly guided to the observation target. In another embodiment, the insertion unit 10a of the scanning medical probe 10 may be inserted into a forceps channel of an electronic-scope so that the tip part of the insertion unit 10a can be guided to the observation target through the forceps channel.

Next, the processor 20 according to the embodiment is explained with reference to FIG. 2. The processor 20 includes a light source unit which supplies illumination light to the scanning medical probe 20, a driving unit which drives the scanning medical probe 10, and a signal processing unit which detects the reflected light obtained by the scanning medical probe 10 and generates an image signal adapted to display on the monitor 30. In this embodiment, the processor 20 is configured as an all-in-one processor in which the light source unit, the driving unit and the signal processing unit are provided. However, in another embodiment, a part of or all of the light source unit, the driving unit and the signal processing unit may be configured as separate units.

The light source unit of the processor 20 includes laser sources 230R, 230G and 230B which emit laser beams respectively corresponding to wavelengths of R, G and B color components, drivers 232R, 232G and 232B which drive the laser sources 230R, 230G and 230B, respectively, and a laser coupler 234. By thus using the laser sources of the wavelengths of the R, G and B color components, a color image is generated. However, in another embodiment, in order to generate a color image, a single white fiber laser source which emits wideband supercontinuum light may be used as a light source.

The driving unit of the processor 20 is configured by the X-axis driver 220X and the Y-axis driver 220Y which drive the actuator 112 of the scanning medical probe 10. Under control of a timing controller 240, the X-axis driver 220X and the Y-axis driver 220Y apply predetermined driving voltages to the actuator 112 via the conductive wires (not shown).

The signal processing unit of the processor 20 includes a laser divider 254, detectors 250R, 250G and 250B, A-D converters 252R, 252G and 252B, a signal processing circuit 260 and an encoder 270. The laser divider 254 divides the reflected light being transmitted through the light-receptive fibers 120 into light having a wavelength of an R component, light having a wavelength of G component and light having a wavelength of B component. The detectors 250R, 250G and 250B receive the R component light, the G component light and the B component light, respectively. The A-D converters 252R, 252G and 252B execute A-D conversion on output signals from the detectors 250R, 250G and 250B, respectively. The signal processing circuit 260 executes predetermined signal processing on the A-D converted signals. The encoder 270 converts the processed signals into a video signal, and outputs the video signal to the monitor 30.

Further, the processor 20 includes a light amount control circuit 280 which controls the light amount of laser light emitted by each of the laser sources 230R, 230G and 230B. The light amount control circuit 280 executes a light amount control process which is described later so that the amount of laser light emitted from each of the laser sources 230R, 230G and 230B can be changed by controlling the driver 232R, 232G and 232B. The timing controller 240 provided in the processor 20 totally controls timings of various processes executed by the components in the processor 20.

Hereafter, a flow of observation of a body cavity conducted by the medical observation system 1 is explained with explanation regarding operations of the components. When the processor 20 is turned ON, the timing controller 240 outputs driving signals to the drivers 232R, 232G and 232B. The drivers 232R, 232G and 232B drive the laser sources 230R, 230G and 230B, respectively, in accordance with the driving signals. The laser sources 230R, 230G and 230B respectively emit the R component light, G component light and B component light.

The laser light emitted from each of the laser sources 230R, 230G and 230B is input to the laser coupler 234. The laser coupler 234 has, for example, dichroic mirrors, by which the R component light, the G component light and the B component light are coupled. Although in FIG. 2 optical path lengths of the R component light, the G component light and the B component light are illustrated as if the optical path lengths are different from each other for the purpose of illustration, in practice the optical path lengths are equal to each other. The laser light (hereafter, frequently referred to as scanning light) coupled by the laser coupler 234 is converged by a coupling lens 234a, and proceeds toward the SMF 110. It should be noted that the laser coupler 234 may not be formed of dichroic mirrors, but may be configured such that laser sources coupled by optical fibers are connected to an optical combiner or an optical waveguide. If a single white fiber laser is used as a light source, white laser emitted from the light source may be directly converged by the coupling lens 234a without using the laser coupler 234, and may be emitted toward the SMF 110. The laser light inputted to the SMF 110 is transmitted through the SMF 110, and is emitted from the exit end face 110a of the SMF 110 at the tip part of the insertion unit 10a of the scanning medical probe 10.

In synchronization with the above described activation of the light source unit, the timing controller 240 outputs driving signals for driving the actuator 112 to the X-axis driver 220X and the Y-axis driver 220Y. The X-axis driver 220X and the Y-axis driver 220Y drive the actuator 112 in accordance with the received driving signals. Specifically, the X-axis driver 220X applies a first alternating voltage to the actuator 112 based on the received driving signal, and the Y-axis driver 220Y applies, to the actuator 112, a second alternating voltage which has the same frequency as that of the first alternating voltage and has the phase orthogonal to the phase of the first alternating voltage.

Figure 3:
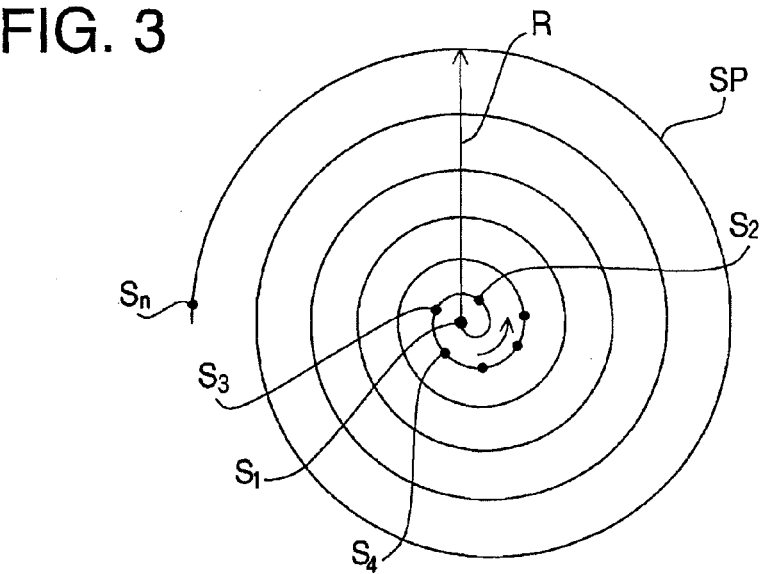
FIG. 3 illustrates a scanning pattern formed by the scanning medical probe according to the embodiment of the invention.

The actuator 112 oscillates in accordance with the first and second alternating voltages applied by the X-axis driver 220X and the Y-axis driver 220Y. The oscillation of the actuator 112 produces an oscillating motion of the tip part of the SMF 110. The exit end face 110a of the SMF 110 moves to draw a circular track having a predetermined radius on a plane nearly equal to the X-Y plane by combined kinetic energy of kinetic energy in the X-direction and kinetic energy in the Y-direction by the actuator 112. By causing the SMF 110 to oscillate while changing the amplitudes of the driving voltages from the X-axis driver 220X and the Y-axis driver 220Y, the tip part of the SMF 110 is moved spirally from the center toward the outside. As a result, as shown in FIG. 3, the scanning light is emitted from the exit end face 110a to draw a spiral scanning pattern toward the observation target.

During a period (hereafter, referred to as a "scanning pattern period") between a time when the application of the first and second alternating voltages from the X-axis driver 220X and the Y-axis driver 220Y is started and a time when the exit end face 110a of the SMF 110 finishes drawing the circular track having the predetermined radius R, the SMF 110 continues to emit the scanning light. The reflected light received during the scanning pattern period is obtained as an image for one frame. When the SMF 110 has moved to a state of drawing the circular track having the predetermined radius R, application of the alternating voltages to the actuator 112 is stopped. Then, the amplitude of the oscillating motion of the tip part of the SMF 110 gradually reduces. With gradual reduction of the oscillation of the tip part of the SMF 110, the exit end face 110a of the SMF 110 gradually approaches the center of the circular track while drawing a spiral track. Finally, the exit end face 110a of the SMF 110 stops at the position on the center axis AX. A period between a time when application of the alternating voltages to the actuator 112 is stopped and a time when the exit end face 110a of the SMF 110 stops at the center axis AX is referred to as a "braking period".

A time that elapses before the SMF 110 has moved to the state where the exit end face 110a draws the circular track having the predetermined radius R from the stopped state of the exit end face 110a of the SMF 110 (i.e., the time between start of the scanning pattern period and end of the scanning pattern period) is a known value. In addition, a time that elapses before the exit end face 110a of the SMF 110 stops at the center axis AX from a time of stopping of application of the alternating voltages to the actuator 112 (i.e., a time between start of the braking period and end of the braking period) is also a known value. Furthermore, the position of the exit end face 110a of the SMF 110 during the scanning pattern period is also a known value. Therefore, based on the above described known values, the timing controller 240 is able to repeatedly conduct the timing control for the X-axis driver 220X and the Y-axis driver 220Y (i.e., the timing control for applying and stopping of the alternating voltages with respect to the actuator 112), and the timing control for the drivers 232R, 232G and 232B in a cycle corresponding to one frame (i.e., the timing control of applying and stopping of the driving voltages to each laser source during the scanning pattern period).

The reflected light obtained by scanning on the observation target is received by the light-receptive fibers 120. The reflected light is transmitted through the light-receptive fibers 120, and is coupled at the joint part 10c of the scanning medical probe 10. Then, the reflected light is transmitted to the processor 20. In the processor 20, the reflected light transmitted from the light-receptive fibers 120 is divided into the R component light, the G component light and the B component light, for example, by the dichroic mirrors in the laser divider 254. The R component reflected light, the G component reflected light and the B component reflected light divided by the laser divider 254 enter the detector 250R, 250G and 250B, respectively. The scanning light supplied from the light source unit is guided by the single SMF 110 and is reflected by the observation target. Therefore, the light amount of the reflected light is extremely small. In order to detect such extremely weak light securely and in a low noise level, each of the detectors 250R, 250g and 250B is formed of a high sensitivity photodetector, such as PMT (Photomultiplier Tube).

Each of the detectors 250R, 250G and 250B executes photoelectric conversion with respect to the detected light to generate an analog signal. The analog signals generated by the detectors 250R, 250G and 250B are output to the A-D converters 252R, 252G and 252B, respectively. Under control of the timing controller 240, the A-D converters 252R, 252G and 252B sample and hold the analog signals output by the detectors 250R, 250G and 250B, respectively, and convert the sampled and held signals into image data corresponding to spots $S_1, S_2, S_3, \ldots$. The image data converted by the A-D converters 252R, 252G and 252B are then output to the signal processing circuit 260.

The image processing circuit 260 processes the image data to correct pixel positions in accordance with a display format of the monitor 30. Specifically, pixel data obtained with the spiral scanning pattern by the scanning medical probe 10 is stored temporarily in a frame memory while being associated with pixel addresses defined on the solid state imaging device. In the image processing circuit 260, a conversion table in which times T corresponding to spots are associated with pixel addresses has been stored in advance. The conversion table is created based on known information, such as a formation position and a formation time of each spot during the scanning pattern period and the sampling frequency. When the image data (i.e., image data of the R component, image data of the G component and image data of the B component) corresponding to a certain time T is input to the signal processing circuit 260, the signal processing circuit 260 specifies a pixel address of the input image data based on the conversion table.

Figure 4:
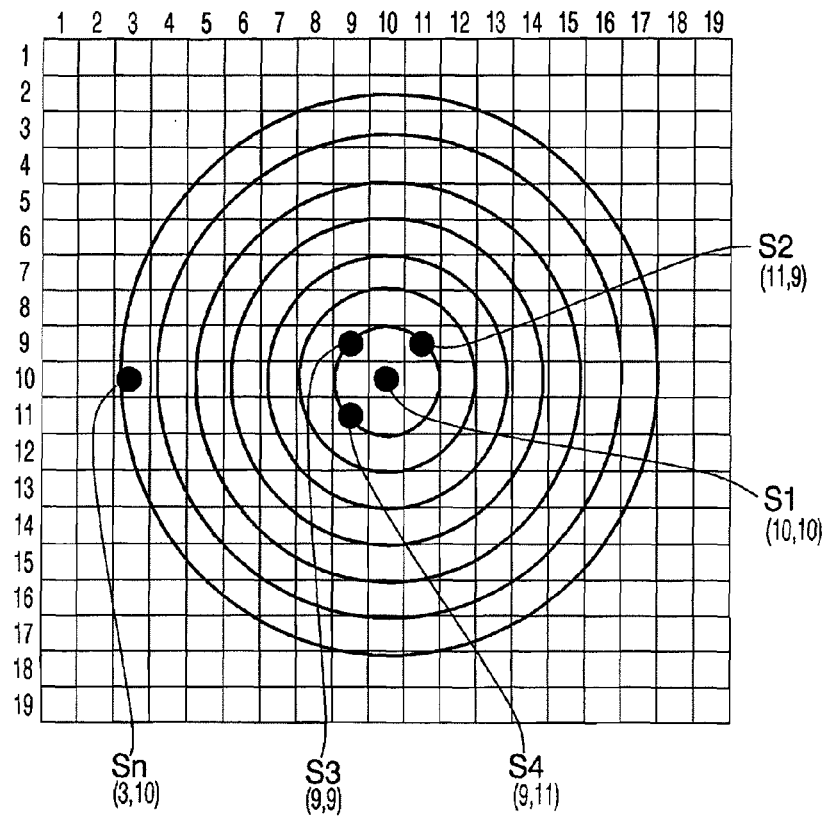
FIG. 4 is an explanatory illustration for explaining a pixel position correction process by a signal processing circuit of the processor according to the embodiment of the invention.

Hereafter, a pixel position correction process executed by the image processing circuit 260 is explained with reference to FIG. 4. Let us consider the case where the image data is assigned to the pixel addresses of 19×19 for convenience of explanation. For example, when the image data of the time t1 corresponding to spot S1 is inputted, the image processing circuit 260 refers to the conversion table and stores the image data at the pixel address (10,10). Next, when the image data of the time t2 corresponding to spot S2 is inputted, the image processing circuit 260 refers to the conversion table and stores the image data at the pixel address (11,9). Thus, the image processing circuit 260 specifies the pixel address for the image data which is sequentially inputted thereto, and stores the image data sequentially in the frame memory.

As a result, the image data of one frame is stored at respective pixel addresses in the frame memory. That is, the image data of one frame is stored in the frame memory. In the image processing circuit 260, image processing, such as an enhancement process and a gain adjustment process, is executed for the image data. Subsequently, the image data on which the various processes are executed is read from the image processing circuit 260 under control of the timing controller 240, and is input to the encoder 270. The encoder 270 converts the image data into a video signal having a predetermined format, such as NTSC (National Television Standard Committee) or PAL (Phase Alternating Line), and outputs the video signal to the monitor 30. Thus, video of the observation target is displayed on the monitor 30.

Next, a light amount control process executed by the light amount control circuit 280 is explained. As described above, in a typical observation for a body cavity by the medical observation system 1, the scanning light (laser light) is emitted toward an observation target in the state where the insertion unit 10a of the scanning medical probe 10 is inserted in to the body cavity. However, there is a case where the scanning medical probe 10 is placed in an examination room in the state where the scanning light is being emitted from the tip of the insertion unit 10a of the scanning medical probe 10. For this reason, according to the embodiment, when the scanning medical probe 10 is located on the outside of a body of a patient (i.e., when there is a possibility that the laser light emitted from the scanning medical probe 10 directly enters an eye of an operator or an patient), the light amount control process is executed to limit the amount of laser light to be emitted from the laser sources 230R, 230G and 230B. Specifically, under control of the light amount control circuit 280, the drivers 232R, 232G and 232B are controlled to limit the amount of the scanning light emitted from the scanning medical probe 10 to one of three levels A, B and C described below.

Level A (e.g., 5.0 mW): a light amount which is dangerous for straight gaze but is adequate for observation of a body cavity.

Level B (e.g., 1.0 mW): a light amount for which eye protection can be achieved by blinking and which enables diagnostic observation of a body cavity to some extent.

Level C (e.g., lower than or equal to 0.4 mW): a light amount which is not dangerous for straight gaze, but is insufficient for diagnostic observation of a body cavity.

Figure 5:
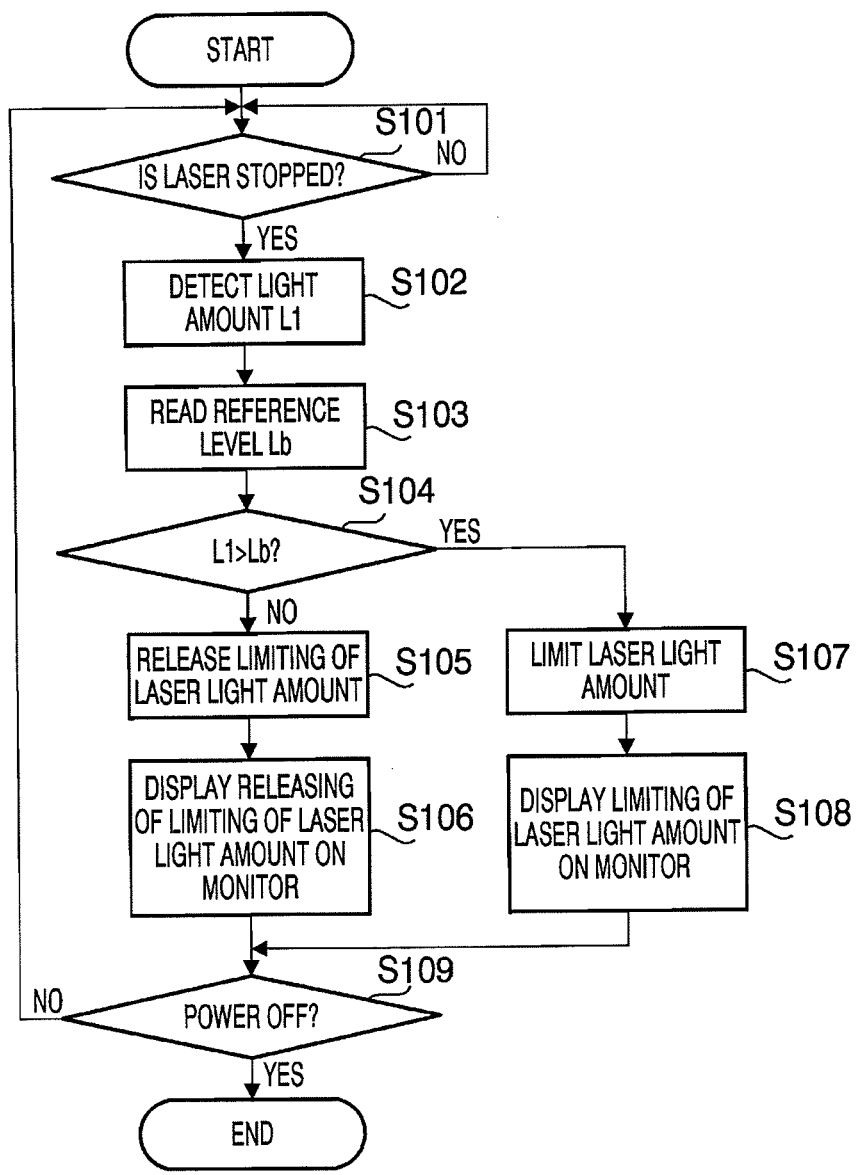
FIG. 5 is a flowchart illustrating a light amount control process according to a first embodiment of the invention.

FIG. 5 is a flowchart illustrating the light amount control process according to the embodiment of the invention. The light amount control process is executed by the light amount control circuit 280, and is started when the processor 10 is turned ON. First, the light amount control circuit 280 judges whether driving of the laser sources 230R, 230G and 230B is stopped (step S101).

Figure 6:
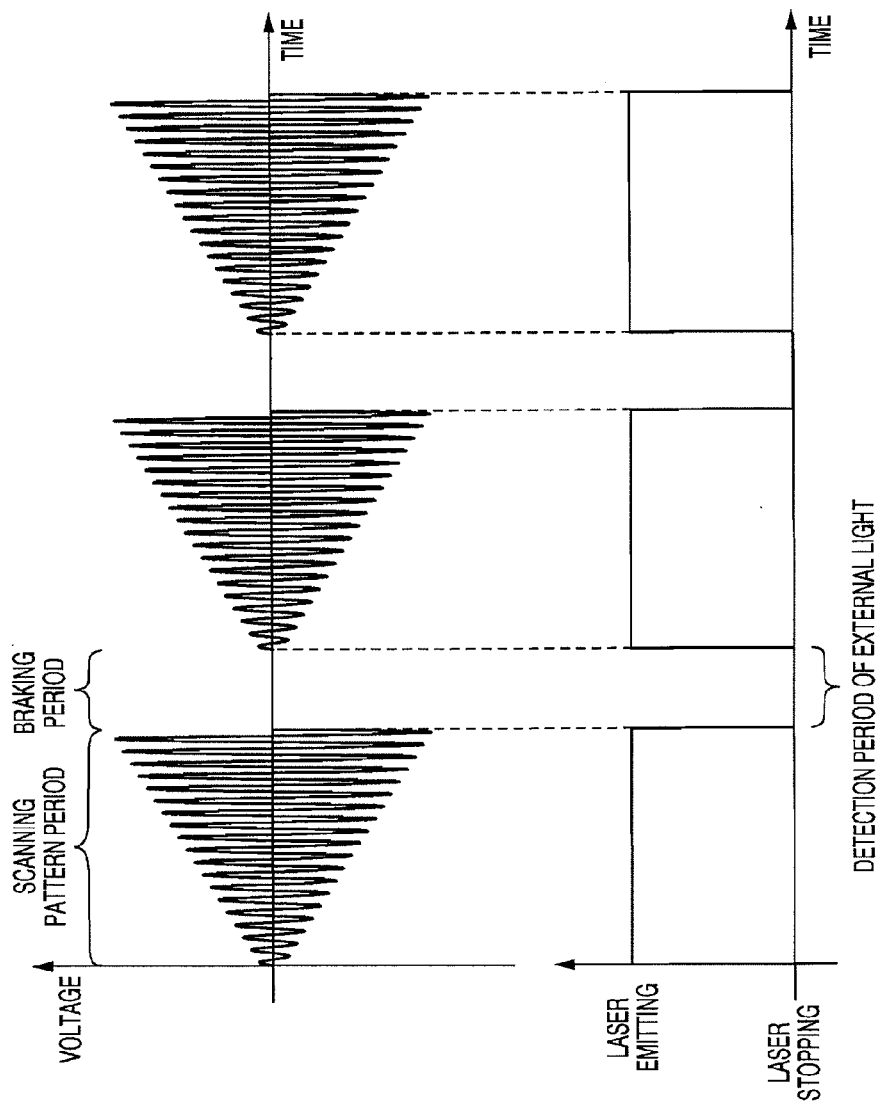
FIGS. 6A and 6B illustrate a timing chart for explaining timing for detection of external light.

FIGS. 6A and 6B show timing charts illustrating timings of driving and stopping of the laser sources 230R, 230G and 230B. Specifically, FIG. 6A is a timing chart of the driving voltage applied to the actuator 112, and FIG. 6B is a timing chart of the driving voltage to be applied to each of the laser sources 230R, 230G and 230B. As described above, during the observation of the body cavity, the timing control for the X-axis driver 220A, the Y-axis driver 220Y, and the drivers 232R, 232G and 232B is executed under control of the timing controller 240.

Specifically, when the frame rate of the scanning medical probe 10 is 30 fps, a total of the scanning pattern period and the braking period for one frame is 33.3 msec. When the scanning pattern period corresponds to 200 spirals and the braking period corresponds to 133 spirals, the scanning pattern period corresponds to 20 msec and the braking period corresponds to 13.3 msec. Therefore, in this case, the timing controller 240 controls and drives the drivers 232R, 232G and 232B so that the scanning light is emitted only in the period of 20 msec. As a result, during the braking period 13.3 msec, riving of the laser sources 230R, 230G and 23B is stopped and thereby emission of the laser light is stopped.

When the laser sources are not stopped (i.e., during the scanning pattern period) (S101: NO), the light amount control circuit 280 waits until the laser sources are stopped. When the laser sources are stopped (S101: YES), the light amount control circuit 280 detects a light amount L1 from the analog signal detected by each of the detectors 250R, 250G and 250B (step S102). As described above, during the braking period, emission of the laser light is stopped. Therefore, the light amount L1 detected in step S102 during the braking period (the period of 13.3 msec) is an amount of light (i.e., external light) other than the laser light received by the light-receptive fibers 120.

Next, the light amount control circuit 280 reads out a reference level Lb stored in a memory (not shown) in the processor 20 (step S103). The reference level Lb represents a light amount corresponding to a back level of the medical observation system 1. The reference level Lb (i.e., the black level) is determined at the time of factory shipment or a time of calibration, and is stored in the memory in advance. Next, the light amount control circuit 280 compares the received light amount L1 with the reference level Lb (step S104). In general, there is no external light in a body cavity of a patient, and therefore no light enters the light-receptive fibers 120 in the state where the scanning medical probe 10 is inserted in the body cavity of the patient and the laser light is not emitted from the scanning medical probe 10. On the other hand, when the scanning medical probe 10 is placed on an outside of a body of a patient, external light, such as room lighting of the examination room, enters the light-receptive fibers 120 even when the laser light is not emitted from the scanning medical probe 10. Therefore, by judging whether the light amount which is received during the braking period is larger than the black reference level, it is possible to judge whether the scanning medical probe 10 has been inserted into a body cavity of a patient.

When the light amount L1 is lower than or equal to the reference level Lb (S104; NO), the light amount control circuit 280 judges that the scanning medical probe 10 has been inserted into a body cavity of a patient, and the limiting of the amount of laser light is released. Thereby, the light amount control circuit 280 controls the drivers 232R, 232G and 232B so that the laser light of the level A is emitted from each of the laser sources 230R, 230G and 230B (step S105). Then, a message indicating that the amount of laser light is not limited is displayed on the monitor 30 (step S106). By displaying the message regarding the limiting of the amount of light, the operator can easily understand the level of the laser light emitted from the scanning medical probe 10.

On the other hand, when the light amount L1 is larger than the reference level Lb (S104: YES), it is judged that the scanning medical probe 10 has not been inserted into a body cavity of a patient. Specifically, the light amount control circuit 280 controls the drivers 232R 232G and 232B so that the laser light of the level B or level C is emitted from each of the laser sources 230R, 230G and 230B (step S107). Then, a message indicating that the amount of laser light is now limited is displayed on the monitor 30 (step S108). Then, steps S101 to S108 are repeatedly processed until the processor 20 is turned OFF (step S109). With this configuration, it becomes possible to appropriately limit the amount of laser light even when the scanning medical probe 10 is used in circumstances where the scanning medical probe 10 is inserted into and withdrawn from a body cavity of a patient by an operator during the observation.

As described above, according to the first embodiment, whether the scanning medical probe 10 has been inserted into a body cavity of a patient is judged based on the amount of light received during the braking period of the scanning medical probe 10. When it is judged that the scanning medical probe 10 has not been inserted into a body cavity of a patient, the amount of laser light is limited to a safety level and thereby it becomes possible to conduct the observation for the body cavity while securing safety even when the laser light emitted from the scanning medical probe 10 directly enters an eye of a person in the examination room such as an operator.

Second Embodiment

Hereafter, a second embodiment of the invention is explained. Since a medical observation system according to the second embodiment has substantially the same configuration as those of the first embodiment shown in FIGS. 1 and 2 and the flow of the observation explained in the first embodiment can also be applied to the second embodiment, in the following explanation focuses on the feature of the second embodiment (i.e., a light amount control process executed by the light amount control circuit 280). In the following, to elements, which are substantially the same as those of the first embodiment, the same reference numbers are assigned, and explanations thereof will not be repeated.

Figure 7:
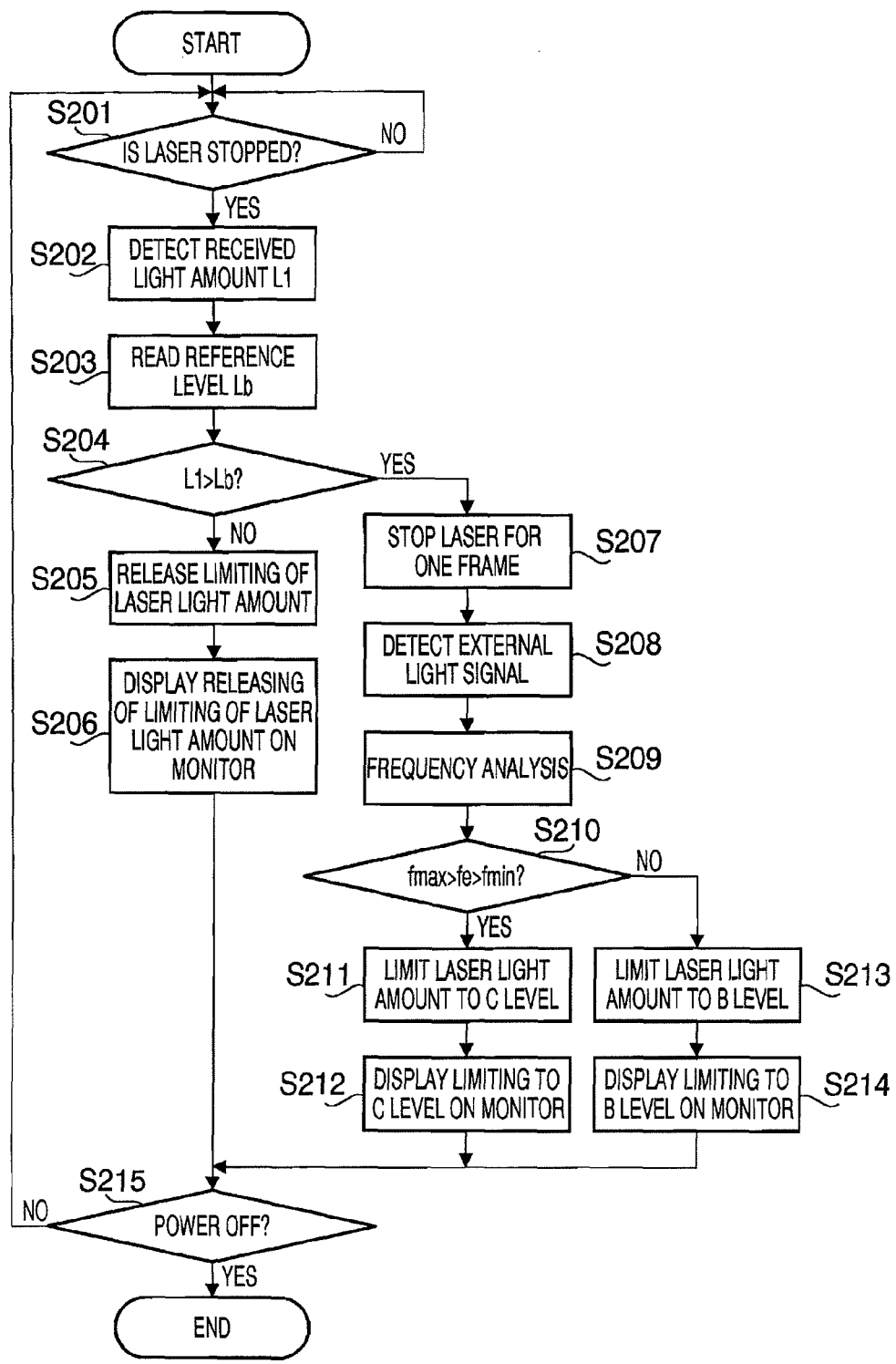
FIG. 7 is a flowchart illustrating a light amount control process according to a second embodiment of the invention.

FIG. 7 is a flowchart illustrating the light amount control process according to the second embodiment. Steps S201 to S206 in the light amount control process according to the second embodiment are the same as steps S101 to S106 of the first embodiment. That is, as in the case of the first embodiment, the reference level Lb and the light amount L1 which is an amount of light received during the braking period of the scanning medical probe 10 are compared (steps S201 to S204). When the light amount L1 is lower than or equal to the reference level Lb (S204; NO), limiting of the amount of laser light is released (step S205), and a message indicating that limiting of the amount of laser light is released is displayed on the monitor 30 (step S206).

On the other hand, when the light amount L1 is larger than the reference level Lb (S204: YES), the light amount control circuit 280 controls the drivers 232R, 232G and 232B to stop driving of the laser sources 230R, 230G and 230B during the scanning pattern period of the subsequent one frame (step S207). In this case, the light received by the light-receptive fibers 120 during the scanning pattern period of the one frame is detected as external light by each of the detectors 250R, 250G and 250B (step S208). Then, frequency analysis is executed on the detected external light to obtain the frequency fe of the external light (step S209).

Figure 8A:
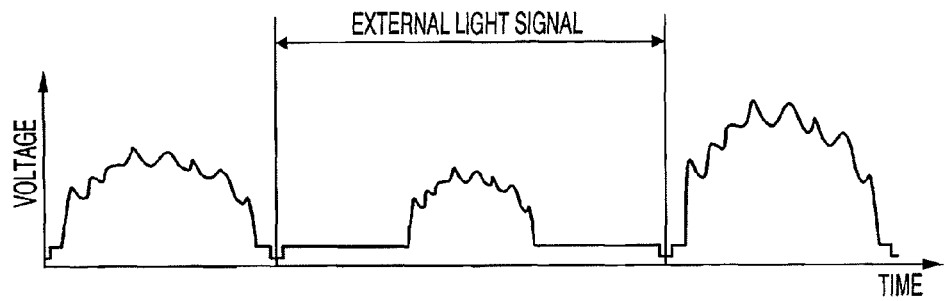
FIGS. 8A-8C illustrate examples of an external light signal detected during a period of stopping of laser light.
Figure 8B:
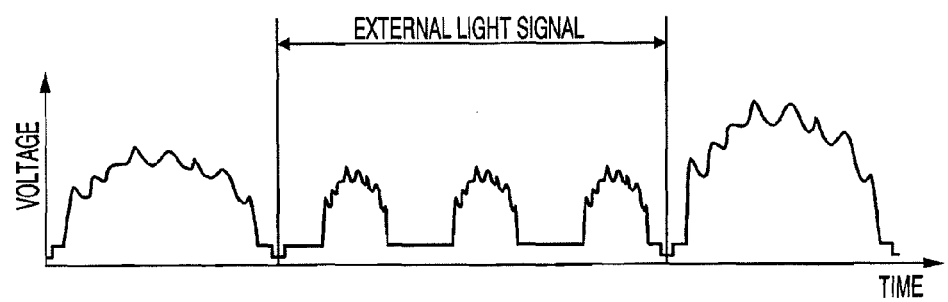
Figure 8C:
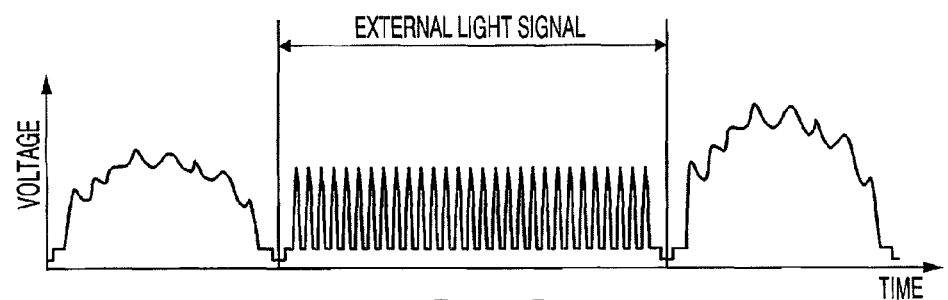

FIGS. 8A-8C illustrate examples of an external light signal. FIG. 8A illustrates an external light signal when light emitted by an incandescent lamp is received, FIG. 8B illustrates an external light signal when light emitted from a fluorescent lamp is received, and FIG. 8C illustrates an external light signal when light emitted from an inverter type fluorescent lamp is received. As shown in FIGS. 8A to 8C, when external light emitted by an incandescent lamp or a fluorescent lamp is received by the light-receptive fiber 120 of the scanning medical probe 10, the light is detected as light which blinks at a predetermined frequency. For example, when the external light from the incandescent lamp is received, the frequency fe of the external light is approximately 50 Hz to 60 Hz. When the external light from the fluorescent lamp is received, the frequency fe of the external light is approximately 100 Hz to 120 Hz. When the external light from the inverter type fluorescent lamp is received, the frequency fe of the external light is approximately 10 kHz to 20 kHz.

Next, the light amount control circuit 280 judges whether the frequency fe obtained in step S209 falls within a range from the upper limit frequency fmax to the lower limit frequency fmin (step S210). The upper limit frequency fmax is an expected maximum frequency of external light, and the lower limit frequency fmin is an expected minimum frequency of the external light. For example, the upper limit frequency fmax is set for 20 kHz which is a frequency of light received from the inverter type fluorescent lamp, and the lower limit frequency fmin is set for 50 Hz which is a frequency of light received from the incandescent lamp.

When the frequency fe falls within the range from the upper limit frequency fmax to the lower limit frequency fmin (S210: YES), the light-receptive fibers 120 are receiving the external light of one of the above described types. Therefore, in this case, the light amount control circuit 280 judges that the scanning medical probe 10 is placed on the outside of the body of the patient, and the amount of laser light is limited. Specifically, the light amount control circuit 280 controls the drivers 2332R, 232G and 232B so that the laser light of the light amount level C is emitted from each of the laser sources 230R, 230G and 230B (step S211). In this case, a message indicating that the amount of laser light is now limited to level C is displayed on the monitor 30 (step S212).

On the other hand, when the frequency fe is outside the range from the upper limit frequency fmax to the lower limit frequency fmin (S210: NO), the light amount L1 of light received by the light-receptive fibers 120 is larger than the reference level, but the external light having the predetermined frequency is not received. For example, the case where the judgment result of S210 is "NO" corresponds to a case where the scanning medical probe 10 is used together with an electronic-scope having an imaging device such as a CCD and the light-receptive fibers 120 of the scanning medical probe 10 receives continuous light such as Xenon light emitted from the electronic-scope, or a case where the light-receptive fibers 120 receive continuous light, such as LED light or sunlight. In the former case, the scanning medical probe 10 is inserted into a body cavity of a patient. In the latter case, the scanning medical probe 10 is on the outside of the body of the patient. In such cases, the light amount control circuit 280 controls the drivers 232R, 232G and 232B so that the laser light of the level B is emitted from each of the laser sources 230R, 230G and 230B (step S213). Further, a message indicating that the amount of laser light is now limited to the level B is displayed on the monitor 30 (step S214). Then, steps S201 to S214 are repeatedly processed until the processor 20 is turned OFF (step S215).

As describe above, in this embodiment, if both of the case where the scanning medical probe 10 is inserted into the body cavity the patient and the case where the scanning medical probe 10 is on the outside of the body of the patient are expected, the amount of laser light is limited to the level B which is a safety level and which allows observation of the body cavity to some extent. Therefore, according to the second embodiment, it is prevented that the amount of laser light is limited and thereby acquisition of the image of the target becomes impossible when the scanning medical probe is in the body cavity of the patient. Such advantages are obtained in addition to the advantages of the first embodiment.

Third Embodiment

Hereafter, a third embodiment of the invention is explained. Since a medical observation system according to the third embodiment has substantially the same configuration as those of the first embodiment shown in FIGS. 1 and 2 and the flow of the observation explained in the first embodiment can also be applied to the third embodiment, in the following explanation focuses on the feature of the third embodiment (i.e., a light amount control process executed by the light amount control circuit 280). In the following, to elements, which are substantially the same as those of the first embodiment, the same reference numbers are assigned, and explanations thereof will not be repeated.

Figure 9:
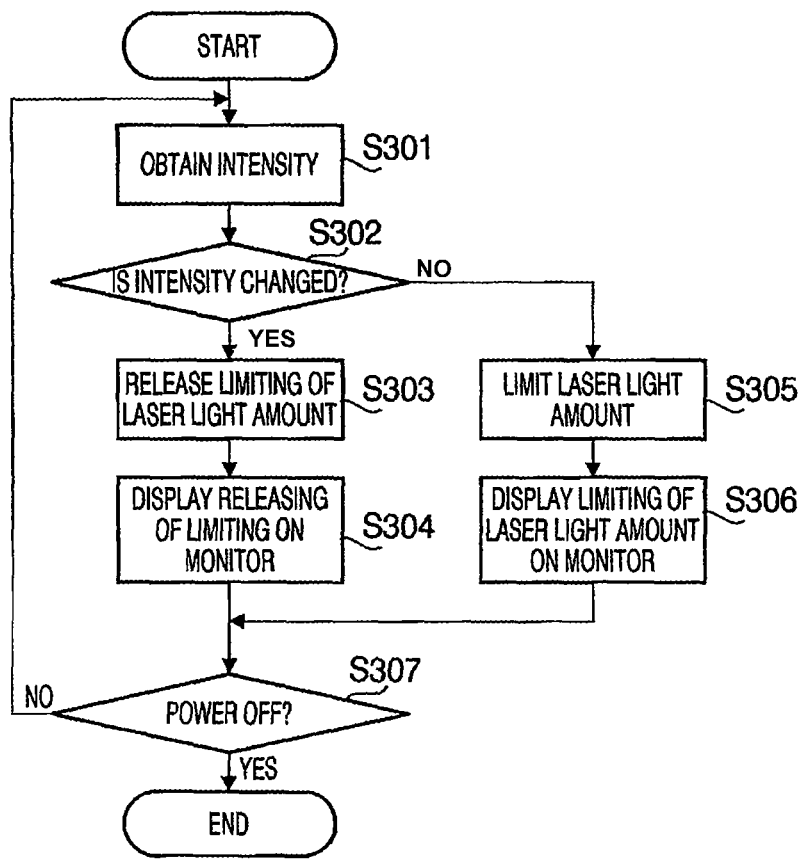
FIG. 9 is a flowchart illustrating a light amount control process according to a third embodiment of the invention.

FIG. 9 is a flowchart illustrating the light amount control process according to the third embodiment. First, an average intensity of an image corresponding to one frame is calculated based on the analog signals detected by the detectors 250R, 250G and 250B (step S301). Then, the light amount control circuit 280 judges whether the calculated average intensity has changed with respect to an average intensity obtained in the immediately previous frame (step S302).

Typically, in a state where the scanning medical probe 10 has been inserted into a body cavity of a patient for observation, the tip part of the scanning medical probe 10 is moved by the operator and therefore the average intensity of the image changes on a frame-by-frame basis. Therefore, when it is judged that the average intensity has changed (S302: YES), it is judged that the scanning medical probe 10 has been inserted in the body cavity of the patient, and limiting of the amount of laser light is released (step S303). That is, in this case, the light amount control circuit 280 controls the drivers 232R, 232G and 232B so that each of the laser sources 232R, 232G and 232B emits the laser light of the level A (S303). Furthermore, a message indicating that limiting of the amount of laser light is not being executed is displayed on the monitor 30 (step S304).

On the other hand, when the scanning medical probe 10 is on the outside of the body of the patient (e.g., when the scanning medical probe 10 is placed in the examination room), the tip part of the scanning medical probe 10 is not moved and the target image stays motionless. Therefore, the intensity does not change on a frame-by-frame basis. Therefore, when it is judged that the average intensity does not change (S302: NO), it is judged that the scanning medical probe 10 has not been inserted into the body cavity of the patient, and therefore the amount of laser light is limited. Specifically, the light amount control circuit 280 controls the drivers 232R, 232g and 232B so that each of the laser sources 230R, 230G and 230B emits the laser light of the level B or C (step S305). In this case, a message indicating that the amount of laser light is being limited is displayed on the monitor 30 (step S306). Then, steps S301 to S306 are repeatedly processed until the processor 20 is turned OFF (step S307).

As described above, according to the third embodiment, whether the scanning medical probe 10 has been inserted into the body cavity of the patient is determined based on the average intensity of the image signal of one frame detected during the observation of the body cavity. By thus making a judgment based on the image signal obtained during normal observation of the body cavity of the patient, it becomes possible to judge whether the scanning medical probe 10 is in a body cavity more accurately. Such advantages can be obtained in addition to the above described advantages of the first embodiment.

Fourth Embodiment

Hereafter, a fourth embodiment is described. FIG. 10A illustrates an outer appearance of a scanning medical probe 10A according to the fourth embodiment. As shown in FIG. 10A, the feature of the scanning medical probe 10A is that a contact sensor 150 is provided at the grip part 10b, and a humidity sensor 160 is provided at the tip of the insertion unit 10a. Since the configuration of the medical scanning probe 10A other than the contact sensor 150 and the humidity sensor 160 is substantially the same as that of the first embodiment shown in FIGS. 1 and 2, in the following the explanation focuses on the feature of the fourth embodiment. In the following, to elements, which are substantially the same as those of the first embodiment, the same reference numbers are assigned, and explanations thereof will not be repeated.

The contact sensor 150 senses contact with a hand of an operator when the operator grips the grip part 10b of the scanning medical probe 10A. The humidity sensor 160 senses humidity in air. In this embodiment, a humidity sensor of a type which becomes a state of being unable to sense humidity in a wet condition is used as the humidity sensor 160. That is, the humidity sensor 160 serves to detect whether the tip of the scanning medical probe 10A is wet. Detection results obtained by the contact sensor 150 and the humidity sensor 160 are transmitted to the light amount control circuit 280 of the processor 20. The light amount control circuit 280 executes a light amount control process based on the detection results of the sensors.

Figure 11:
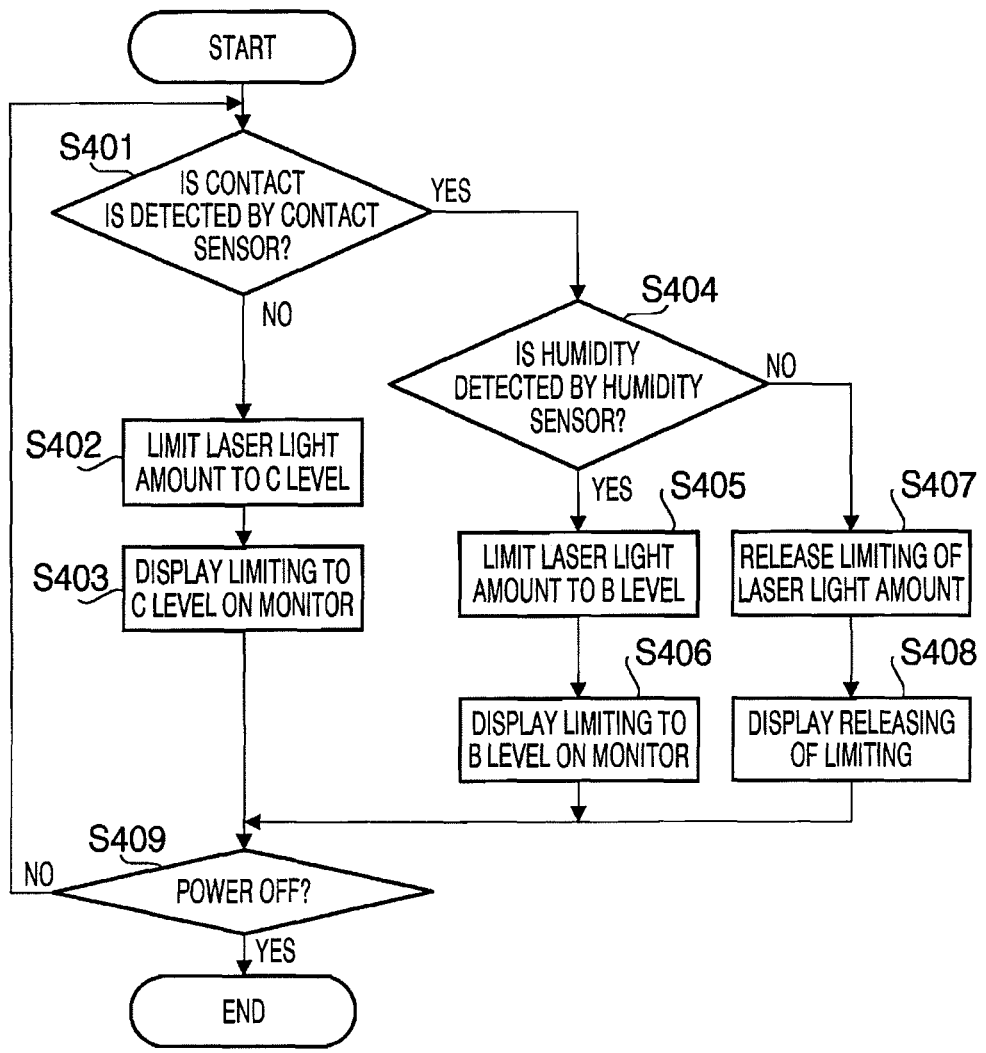
FIG. 11 is a flowchart illustrating a light amount control process according to the fourth embodiment of the invention.

FIG. 11 is a flowchart illustrating the light amount control process according to the fourth embodiment. First, the light amount control circuit 280 judges whether contact with the operator is detected by the contact sensor 150 (step S401). When contact is not detected (S401: NO), the grip part 10b of the scanning medical probe 10A is not gripped by the operator. Therefore, in this case, the light amount control circuit 280 judges that the scanning medical probe 10A is not inserted into a body cavity of a patient, and the amount of laser light is limited. Specifically, in this case, the light amount control circuit 280 controls the drivers 232R, 232G and 232B so that the laser light of the level C is emitted from each of the laser sources 230R, 230G and 230B (step S402). Then, a message indicating that the amount of laser light is now limited to the level C is displayed on the monitor 30 (step S403).

On the other hand, when contact with the operator is detected (S401: YES), it is judged that the scanning medical probe 10A is gripped by the operator. That is, in this case, the scanning medical probe 10A is under control of the operator regardless of whether the scanning medical probe 10A has been inserted into the body cavity of the patient. Then, the light amount control circuit 280 judges whether humidity is detected by the humidity sensor 160 (step S404). As described above, in step S404, the light amount control circuit 280 judges whether the tip of the scanning medical probe 10A is wet in accordance with whether the humidity sensor 160 is normally detecting humidity. In another embodiment, the light amount control circuit 280 may judge whether the tip of the scanning medical probe 10A is wet in accordance with a humidity value detected by a humidity sensor. For example, the light amount control circuit 280 may judge that the tip of the scanning medical probe 10A is wet when the humidity of 100% is detected by a humidity sensor or when the humidity detected by a humidity sensor is higher than or equal to a predetermined value.

When the humidity sensor 160 is normally detecting humidity (S404: YES), it is judged that the tip of the scanning medical probe 10A is not wet. In this case, it is judged that there is a high possibility that the scanning medical probe 10A is not inserted into the body cavity of the patient. Therefore, in this case the amount of laser light is limited. Specifically, the light amount control circuit 280 controls the drivers 232R, 232G and 232B so that the laser light of the level B is emitted from each of the laser sources 230, 230G and 230B (step S405). Further, a message indicating that the amount of laser light is now limited to the level B is displayed on the monitor 30 (step S406).

When the humidity sensor 160 is in the state of being unable to sense humidity (S404: NO), it is judged that the tip of the scanning medical probe 10A is wet. In this case, it is judged that the scanning medical probe 10A has been inserted into the body cavity of the patient, and limiting of the amount of laser light is released (step S407). That is, the light amount control circuit 280 controls the drivers 232R, 232G and 232B so that the laser light of the level A is emitted from each of the laser sources 230R, 230G and 230B (S407). Further, a message indicating that limiting of the amount of laser light is not executed is displayed on the monitor 30 (step S408). Then, steps S401 to S408 are repeatedly processed until the scanning medical probe 10A is turned OFF.

As described above, in the fourth embodiment, the light amount control circuit 280 judges whether the scanning medical probe 10A has been inserted into the body cavity of the patient in accordance with the detected results of the sensors provided in the scanning medical probe 10A. When it is judged that the scanning medical probe 10A is not inserted into the body cavity of the patient, the light amount control circuit 280 reduces the amount of laser light to the safety level. Consequently, it becomes possible to secure safety even in the state where the laser light emitted from the scanning medical probe 10A directly enters an eye of a person in the examination room such as an operator. Furthermore, by conducting the light amount control based on the detection results by the sensors, it becomes possible to reduce the processing load, such as a signal processing, to be put on the processor, and thereby it becomes possible to conduct the light amount control more quickly.

Fifth Embodiment

Hereafter, a fifth embodiment of the invention is described. FIG. 10B illustrates an outer appearance of a scanning medical probe 10B according to the fifth embodiment. As shown in FIG. 10B, the feature of the scanning medical probe 10A is that temperature sensors A, B, C and D are provided at the joint part 10c, the grip part 10b and the insertion unit 10a. Since the configuration of the medical scanning probe 10B other than the temperature sensors A-D is substantially the same as that of the first embodiment shown in FIGS. 1 and 2, in the following the explanation focuses on the feature of the fifth embodiment. In the following, to elements, which are substantially the same as those of the first embodiment, the same reference numbers are assigned, and explanations thereof will not be repeated. Detection results by the temperature sensors A, B, C and D are transmitted to the light amount control circuit 280 of the processor 20. The light amount control circuit 280 executes the light amount control process based on the detection results by the temperature sensors A, B, C and D.

Figure 12:
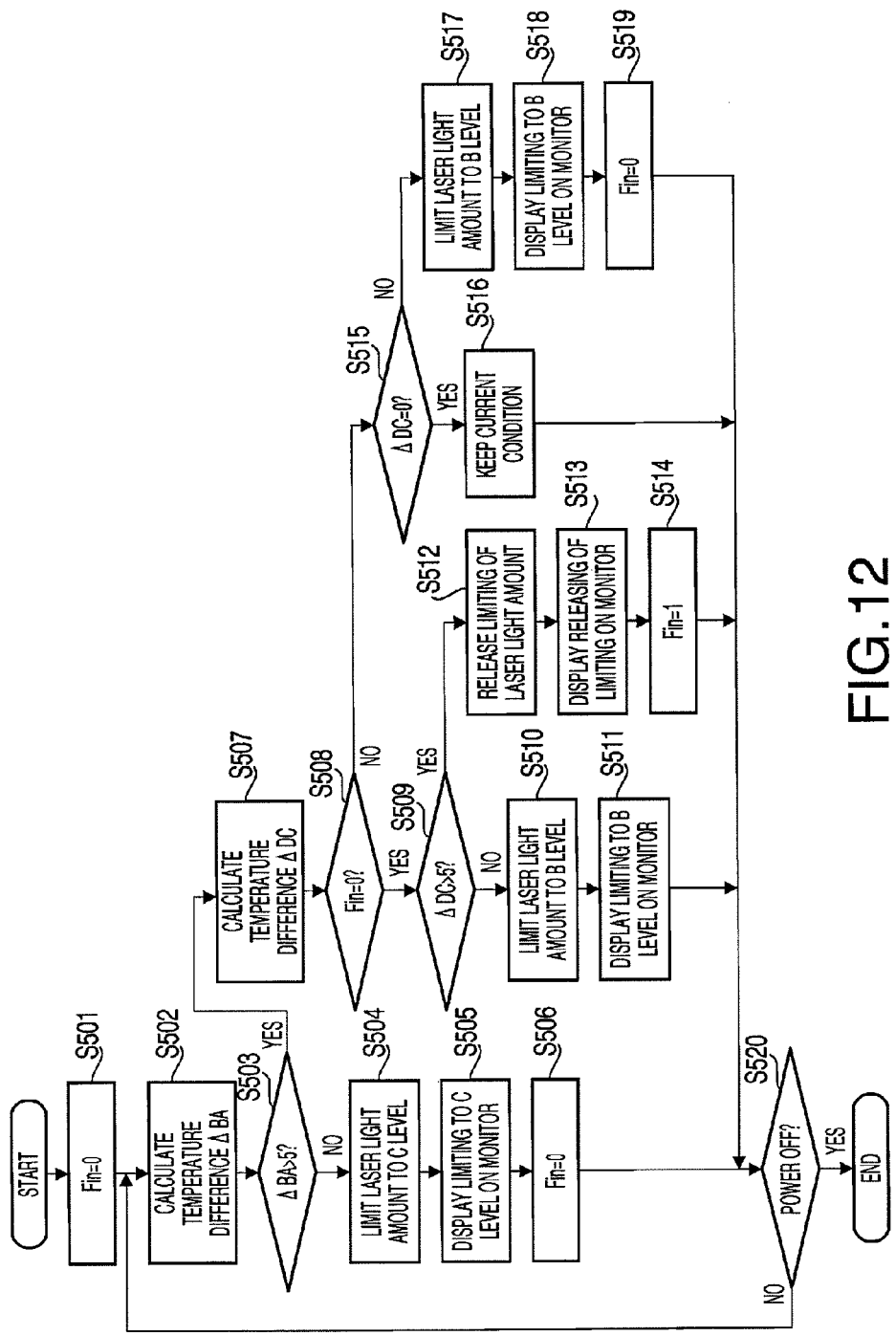
FIG. 12 is a flowchart illustrating a light amount control process according to the fifth embodiment of the invention.

FIG. 12 is a flowchart illustrating the light amount control process according to the fifth embodiment. First, the light amount control circuit 280 sets a parameter Fin to "0" (step S501). The parameter Fin indicates whether the scanning medical probe 10B has been inserted into a body cavity of a patient. The parameter Fin of "0" indicates that the scanning medical probe 10B has not been inserted into the body cavity of the patient, and the parameter Fin of "1" indicates that the scanning medical probe 10B has been inserted into the body cavity of the patient.

Next, based on the detection results of the temperature sensors A and B, the temperature difference ΔBA is calculated (step S502). Specifically, in step S502, the temperature difference ΔBA is obtained by subtracting the temperature detected by the temperature sensor A provided at the joint part 10c from the temperature detected by the temperature sensor B provided at the grip part 10b. Then, the light amount control circuit 280 judges whether the calculated temperature difference ΔBA is larger than 5° (step S503). If the grip part 10b of the scanning medical probe 10B is gripped by the operator, the temperature of the grip part 10b detected by the temperature sensor B becomes lager than the temperature of the joint part 10c detected by the temperature sensor A. Therefore, in step S503, the light amount control circuit 280 judges whether the scanning medical probe 10B is gripped by the operator in accordance with whether the temperature difference between the grip part 10b and the joint part 10c of the scanning medical probe 10B.

When the temperature difference ΔBA is smaller than or equal to 5° C. (S503: NO), the grip part 10b of the scanning medical probe 10B is not gripped by the operator. Therefore, in this case, the light amount control circuit 280 judges that the scanning medical probe 10B has not been inserted into the body cavity of the patient, and executes limiting of the amount of laser light. Specifically, the light amount control circuit 280 controls the drivers 232R, 232G and 232B so that laser light of the level C is emitted from each of the laser sources 230R, 230G and 230B (step S504). Then, a message indicating that the amount of laser light is now limited to the level C is displayed on the monitor 30 (step S505). Next, the parameter Fin which indicates whether the scanning medical probe 10B has been inserted into the body cavity of the patient is set to "0" (step S506).

When the temperature difference ΔBA is larger than 5° (S503: YES), the light amount control circuit 280 judges that the scanning medical probe 10B is now gripped by the operator. In this case, the scanning medical probe 10B is under control of the operator regardless of whether the scanning medical probe 10B has been inserted into the body cavity of the patient. Then, the light amount control circuit 280 calculates the temperature difference ΔDC based on the detection results by the temperature sensors D and C (step S507). Specifically, the temperature difference ΔDC is obtained by subtracting the temperature detected by the temperature sensor C located at a position away by a small distance from the tip of the insertion unit 10a from the temperature detected by the temperature sensor D located at the tip of the insertion unit 10a of the scanning medical probe 10B.

Next, the light amount control circuit 280 judges whether the parameter Fin which indicates whether the scanning medical probe 10B has been inserted into the body cavity of the patient is "0" (step S508). When the parameter Fin is "0" (i.e., the scanning medical probe 10B has not been inserted into the body cavity of the patient) (S508: YES), the light amount control circuit 280 judges whether the calculated temperature difference ΔDC is larger than 5° C. (step S509). It should be noted that when the scanning medical probe 10B is operated to be inserted into the body cavity of the patient from the state where the scanning medical probe 10B is placed in the examination room, the temperature of the tip of the insertion unit 10a increases first. Therefore, when the temperature difference ΔDC is smaller than or equal to 5° C. (S509: NO), there is a high possibility that the scanning medical probe 10B is not inserted into the body cavity of the patient, and limiting of the amount of laser light is executed. Specifically, the light amount control circuit 280 controls the drivers 232R, 232G and 232B so that the laser light of the level B is emitted from each of the laser sources 230R, 230G and 230B (step S510). Then, a message indicating that the amount of laser light is now limited to the level B is displayed on the monitor 30 (step S511).

When the temperature difference ΔDC is larger than 5° C. (S509: YES), it is judged that the scanning medical probe 10B is inserted into the body cavity of the patient, and limiting of the amount of laser light is released. In this case, the light amount control circuit 280 controls the drivers 232R, 232G and 232B so that the laser light of the level A is emitted from each of the laser sources 230R, 230G and 230B (step S512). Then, a message indicating that limiting of the amount of laser light is not executed is displayed on the monitor 30 (step S513). Next, the parameter Fin which indicates whether the scanning medical probe 10B has been inserted into the body cavity of the patient is set to "1" (step S514).

When the parameter Fin is not "0" (i.e., the scanning medical probe 10B has been inserted into the body cavity of the patient) (S508: NO), the light amount control circuit 280 judges whether the temperature difference ΔDC is "0" (step S515). When the temperature difference ΔDC is "0" (S515: YES), there is no temperature difference on the insertion unit 10a. Therefore, in this case, the light amount control circuit 280 judges that the scanning medical probe 10B has been inserted in the body cavity of the patient and the normal observation is now being conducted. Then, the light amount control circuit 280 operates to keep the current condition (step S516). That is, observation under the condition of the amount of laser light of the level A is maintained.

On the other hand, when the scanning medical probe 10B is withdrawn from the body cavity of the patient, the temperature of a part away from the tip of the insertion unit 10a decreases first. Therefore, when the temperature ΔDC is not "0" (S515: NO), it is judged that there is a high possibility that the scanning medical probe 10B is withdrawn from the body cavity of the patient, and in this case the amount of laser light is limited. Specifically, the light amount control circuit 280 controls the drivers 232R, 23G and 23B so that the laser light of the level B is emitted from each of the laser sources 230R, 230G and 230B (step S517). Then, a message indicating that the amount of laser light is now limited to the level B is displayed on the monitor 30 (step S518). Then, the parameter Fin which indicates whether the scanning medical probe 10B has been inserted into the body cavity of the patient is set to "0" (step S519). Steps S501 to S519 are repeatedly processed until the processor 20 is turned OFF (step S520).

As described above, in the fifth embodiment, the light amount control circuit 280 judges whether the scanning medical probe 10B has been inserted into the body cavity of the patient in accordance with the detection results of the sensors provided in the scanning medical probe 10B. When it is judged that the scanning medical probe 10B has not been inserted into the body cavity of the patient, the light amount control circuit 280 reduces the amount of laser light to the safety level. Consequently, it becomes possible to secure safety even in the state where there is a possibility that the laser light emitted from the scanning medical probe 10B directly enters an eye of a person in the examination room such as an operator. Since the light amount control is executed based on the detection results of the sensors, the processing load to be put on the processor 20 can be reduced as in the case of the fourth embodiment. Furthermore, by limiting the light amount by detecting, based on the temperature difference between the detected temperatures by the temperature sensors, the condition of the scanning medical probe 10B immediately before the scanning medical probe 10B is withdrawn from the body cavity of the patient, it is possible to secure safety even if a person in the examination room such as an operator directly looks at the laser light emitted by the tip of the scanning medical probe 10B immediately after the scanning medical probe 10B has been withdrawn from the body cavity of the patient.

Although the present invention has been described in considerable detail with reference to certain preferred embodiments thereof, other embodiments are possible. For example, although in the above described embodiments the scanning medial probe is configured to scan the laser light by producing resonance in a single optical fiber, the present invention is not limited to such a configuration. It is understood that the present invention can also be applied to a medical probe configured to emit laser light in another way.

In the above described first and second embodiments, the light amount control circuit judges whether the scanning medical probe 10 has been inserted into the body cavity of the patient based on the light amount and the frequency of the light detected during the laser stopping period. However, the present invention is not limited to such a configuration. For example, the light amount control circuit may judge whether the scanning medical probe has been inserted into the body cavity of the patient based on the color distribution of light detected during the laser stopping period. In this case, when light having a particular color distribution which is not expected in the normal observation of a body cavity is detected, the light amount control circuit may judge that the scanning medical probe is on the outside of the body of the patient. Specifically, in the normal observation of a body cavity, light having a larger amount in R component is detected. By contrast, a certain type of room lighting, such a fluorescent lamp employing an LED, is configured to generate high intensity white light by mixing blue light and yellow light. If the light detected during the laser stopping period has a larger amount in B component, the light amount control circuit may judge that the scanning medical probe is on the outside of the body of the patient.

In the above described embodiments, the scanning medical probe repeats the scanning pattern period and the braking period while drawing a spiral scanning patter. However, the present invention can also be applied to the case where the scanning medical probe is continuously driven to draw Lissajou's figure. In this case, emission of laser light may be stopped to detect external light at a predetermined timing (e.g., at a timing corresponding to an area where many tracks drawn by the scanning medical probe overlap with each other or a timing of once every 30 frames).

This application claims priority of Japanese Patent Application No. P2009-166880, filed on Jul. 15, 2009. The entire subject matter of the application is incorporated herein by reference.

What is claimed is:

1. A medical observation system, comprising:
a medical probe that is configured to observe a subject by scanning the subject with laser light for a plurality of frames, each frame including a pattern scanning period and a braking period, which follows the pattern scanning period;
a laser source that supplies the laser light to the medical probe;
a light guiding member configured to guide the laser light supplied by the laser source to an exit end face of the light guiding member;
an oscillator configured to oscillate a part of the light guiding member around the exit end face of the light guiding member from a first predetermined position to a second predetermined position in the pattern scanning period, to scan the subject with the laser light;
a judger configured to judge that the medical probe is located outside a body of a patient based on an amount of light, which is received by a light-receptive member, during the braking period, the braking period being a period in which the laser light is not emitted toward the subject and the exit end face of the light guiding member returns from the second predetermined position to the first predetermined position before the pattern scanning period in a subsequent frame starts; and
a controller configured to limit an amount of laser light emitted from the laser source in the subsequent frame to be lower than or equal to a predetermined amount in response to the judger judging that the medical probe is located outside the body.

2. The medical observation system according to claim 1, wherein the controller is configured to reduce the amount of laser light emitted from the laser source in incremental steps based on a result of the judgment by the judger.

3. The medical observation system according to claim 1, wherein the light-receptive member is configured to receive reflected light from the subject.

4. The medical observation system according to claim 1, wherein the judger is further configured to judge that the medical probe is located outside the body when the light amount of the light received by the light-receptive member is larger than a predetermined light amount.

5. The medical observation system according to claim 1, wherein the judger is further configured to judge that the medical probe is located outside the body when the light received by the light-receptive member blinks at a frequency which falls within a predetermined frequency range.

6. The medical observation system according to claim 1, wherein the judger is further configured to judge that the medical probe is located outside the body when an intensity of a signal based on the light received by the light-receptive member does not change.

7. The medical observation system according to claim 1, wherein:
the medical probe includes at least one sensor that detects an ambient condition of the medical probe; and
the judger is further configured to judge that the medical probe is located outside the body based on a detection result by the sensor.

8. The medical observation system according to claim 7, wherein the at least one sensor comprises a plurality of sensors including:
a humidity sensor provided at a tip of the light guiding member; and
a contact sensor provided at a grip part of the medical probe,
wherein the judger is further configured to judge that the medical probe is located outside the body based on detection results by the humidity sensor and the contact sensor.

9. The medical observation system according to claim 7, wherein:
the at least one sensor includes a plurality of temperature sensors; and
the judger is further configured to judge that the medical probe is located outside the body based on a difference between temperatures detected by the plurality of temperature sensors.

10. A non-transitory light amount control circuitry providing instructions that, when executed by a processor, perform the operations comprising:
supplying laser light emitted from a laser source to a medical probe which observes a subject by scanning the subject with the laser light for a plurality of frames, each frame including a pattern scanning period and a braking period, which follows the pattern scanning period, the medical probe including a light guiding member configured to guide the laser light supplied by the laser source to an exit end face of the light guiding member, and an oscillator configured to oscillate a part of the light guiding member around the exit end face of the light guiding member from a first predetermined position to a second predetermined position in the pattern scanning period, to scan the subject with the laser light;
judging that the medical probe is located outside a body of a patient based on an amount of light, which is received by a light-receptive member, during a braking period, the braking period being a period in which the laser light is not emitted toward the subject and the exit end face of the light guiding member returns from the second predetermined position to the first predetermined position before the pattern scanning period in a subsequent frame starts; and
limiting an amount of laser light emitted from the laser source in the subsequent frame to be lower than or equal to a predetermined amount in response to the judging that the medical probe is located outside the body.

11. The non-transitory light amount control circuitry according to claim 10, wherein the limiting reduces the amount of laser light emitted from the laser source in the subsequent frame in incremental steps based on a result of the judging.

12. The non-transitory light amount control circuitry according to claim 10, wherein the judging further judges that the medical probe is located outside the body when the light amount of the light received by the light-receptive member is larger than a predetermined light amount.

13. The non-transitory light amount control circuitry according to claim 10, wherein the judging further judges that the medical probe is located outside the body when the light received by the light-receptive member blinks at a frequency which falls within a predetermined frequency range.

14. A medical observation system, comprising:
a medical probe that is configured to observe a subject by scanning the subject with laser light for a plurality of frames, each frame including a pattern scanning period and a braking period, which follows the pattern scanning period;
a laser source that supplies the laser light to the medical probe;
a light guiding member configured to guide the laser light supplied by the laser source to an exit end face of the light guiding member;
an oscillator configured to oscillate a part of the light guiding member around the exit end face of the light guiding member from a first predetermined position to a second predetermined position in the pattern scanning period, to scan the subject with the laser light;
a judger configured to judge whether the medical probe is in a first state, a second state and a third state, based on an amount and a frequency of light, which is received by a light-receptive member, during the braking period, the braking period being a period in which the laser light is not emitted toward the subject and the exit end face of the light guiding member returns from the second predetermined position to the first predetermined position before the pattern scanning period in a subsequent frame starts; and
a controller configured to control the laser source to limit a light amount of a scanning light emitted from the medical probe in the subsequent frame to one of a first power level, a second power level and a third power level, based on a result of the judgment by the judger, the first power level being a level dangerous to observe but providing an adequate diagnostic image, the second power level being a level less dangerous to observe than the first level but providing an adequate diagnostic image to some extent, the third power level being a level safe to observe but not providing a useful diagnostic image.

* * * * *